United States Patent [19]

Grollier

[11] Patent Number: 5,373,006
[45] Date of Patent: Dec. 13, 1994

[54] COMBINATION OF DERIVATIVES OF 1,8-HYDROXY AND/OR ACYLOXY ANTHRACENE OR ANTHRONE AND OF PYRIMIDINE DERIVATIVES FOR INDUCING AND STIMULATING HAIR GROWTH AND REDUCING LOSS THEREOF

[75] Inventor: Jean F. Grollier, Paris, France
[73] Assignee: L'Oreal, Paris, France
[21] Appl. No.: 995,538
[22] Filed: Dec. 23, 1992

Related U.S. Application Data

[63] Continuation of Ser. No. 278,729, Dec. 2, 1988, abandoned.

[30] Foreign Application Priority Data

Dec. 4, 1987 [LU] Luxembourg ............ 87066

[51] Int. Cl.$^5$ .............. A61K 7/06; A61K 31/54
[52] U.S. Cl. .................. 514/275; 514/256; 514/210; 514/212; 514/252; 514/235.8
[58] Field of Search .................. 514/222, 256

[56] References Cited

U.S. PATENT DOCUMENTS 4,139,619 2/1979 Chidsey, III ............ 424/45

FOREIGN PATENT DOCUMENTS 260010 11/1986 Japan ................ 514/256
2085442 4/1982 United Kingdom ........ 514/212
2184721 7/1987 United Kingdom ........ 514/212

OTHER PUBLICATIONS

The Merck Index, 1976, Ninth Edition, pp. 93 and 94.

Primary Examiner—Dale R. Ore
Attorney, Agent, or Firm—Jacobson, Price, Holman & Stern

[57] ABSTRACT

A composition comprising a combination intended to induce and to stimulate hair growth and to reduce its loss, characterized in that it comprises:
(a) a component (A) containing at least one derivative of 1,8-dihydroxy-, 1,8-diacyloxy- or 1-hydroxy-8-acyloxyanthracene or anthrone, in a physiologically acceptable medium,
(b) a component (B) containing, in a physiologically acceptable medium, at least one pyrimidine derivative corresponding to the formula:

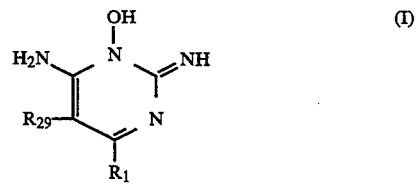

(I)

in which $R_1$ denotes a group

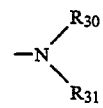

in which $R_{30}$ and $R_{31}$ may, independently of each other, denote hydrogen or an alkyl, alkenyl, alkylaryl or cycloalkyl group; $R_{30}$ and $R_{31}$ can also conjointly, with the nitrogen atom to which they are bonded form a heterocyclic ring chosen from aziridinyl, azetidinyl, pyrrolidinyl, piperidyl, hexahydroazeopinyl, heptamethyleneimine, octamethyleneimine, morpholinyl and 4-(lower)alkylpiperazidinyl groups, it being possible for the heterocyclic groups to be substituted on the carbon atoms by 1 to 3 lower alkyl, hydroxyl or alkoxy groups; the group $R_{29}$ denoting a hydrogen atom or an alkyl, alkenyl, alkylalkoxy, cycloalkyl, aryl, alkylaryl, arylalkyl, alkylarylalkyl, alkoxyarylalkyl or haloarylalkyl group, as well as the salts of addition to physiologically acceptable acids, the components (A) and (B) being present in a sole composition or being intended for separate applications, either simultaneous or successive or spaced in time, to hair and to the scalp.

23 Claims, No Drawings

COMBINATION OF DERIVATIVES OF 1,8-HYDROXY AND/OR ACYLOXY ANTHRACENE OR ANTHRONE AND OF PYRIMIDINE DERIVATIVES FOR INDUCING AND STIMULATING HAIR GROWTH AND REDUCING LOSS THEREOF

This application is a continuation of application Ser. No. 07/278,729, filed Dec. 2, 1988 now abandoned.

The invention relates to the combination of derivatives of 1,8-hydroxy and/or acyloxy anthracene or anthrone and of pyrimidine derivatives with a view to inducing and stimulating hair growth and reducing loss thereof.

Man has a head growth of 100,000 to 150,000 hairs and it is normal to lose 50 to 100 hairs daily. The retention of this head growth results essentially from the fact that the life of a hair is subject to a cycle known as a pilary cycle, during which the hair forms, grows and falls out before being replaced by a new hair which appears in the same follicle.

Three phases are observed successively in the course of a pilary cycle, namely: the anagen phase, the catagen phase and the telogen phase.

During the first phase, known as anagen, the hair passes through a period of active growth associated with an intense metabolic activity in the bulb region.

The second phase, known as catagen, is transitory and is marked by a slowing down of the mitotic activities. During this phase, the hair undergoes an involution, the follicle atrophies and its dermal implantation appears increasingly high.

The final phase, known as telogen, corresponds to a period of rest of the follicle and the hairs ends by falling out, pushed out by a nascent anagen hair.

This process of continual physical renewal undergoes a natural evolution in the course of aging, the hair becomes finer and its cycles being shorter.

Alopecia takes place when this process of physical renewal is accelerated or perturbed, that is to say when the phases of growth are shortened, the transition of the hair to a telogen phase is more precocious and the hair falls out in increasing numbers. The successive growth cycles produce hair which is increasingly finer and increasingly shorter, becoming gradually transformed into an unpigmented down, which can lead to baldness.

Among alopecias, acquired, noncicatricial and diffuse alopecias, such as androgenetic or androgenic alopecia, are particularly difficult to treat, in contrast to localized alopecias such as pelade, which would appear to be immunological in origin.

It has already been proposed in the past to treat pelade with anthralin or 1,8,9-trihydroxyanthracene, producing a nonallergic inflammatory dermatitis; on the other hand, its use in the field of androgenetic alopecia has not been found satisfactory.

Furthermore, it has also been proposed to employ compounds such as 6-amino-1,2-dihydro-1-hydroxy-2-imino-4-piperidinopyrimidine or minoxidil in compositions which make it possible to reduce or to suppress the effect of alopecia and to induce and to stimulate hair growth and to reduce its loss.

The Applicant has now found that, when derivatives of 1,8-hydroxy and/or acyloxy anthracene or anthrone are combined with certain pyrimidine derivatives, an improved induction and stimulation of hair growth is surprisingly observed, together with an effect on the retardation of hair loss.

The effectiveness is characterized more particularly by an activity which is superior in comparison with derivatives of pyrimidine or of 1,8-hydroxy and/or acyloxy anthracene or anthrone when employed by themselves, or else by a more rapid action of the combination with regard to the treatment of hair loss or by a use of the pyrimidine derivative at a lower concentration, particularly in the case of diffuse alopecias.

In order to determine the effectiveness or the speed of action of the compositions for treating alopecia, use is generally made of the trichogram and especially the phototrichogram, which makes it possible to determine, among other things, the percentage of hair in an anagen phase relative to the hair in a telogen phase.

A subject matter of the invention consists, therefore, of the combination of derivatives of 1,8-hydroxy and/or acyloxy anthracene or anthrone with pyrimidine derivatives with a view to inducing or stimulating hair growth and reducing its loss.

Another subject of the invention consists of the cosmetic and/or pharmaceutical compositions containing these compounds.

A further subject of the invention is the devices with a number of compartments containing, in one compartment, the derivative of 1,8-hydroxy and/or acyloxy anthracene or anthrone, and in the other, the pyrimidine derivative, with a view to mixing immediately before the use or applications which are simultaneous, successive or well spaced in time.

Other subjects of the invention will become apparent on reading the description and the examples which follow.

The combination in accordance with the invention is characterized essentially by the fact that is consists of:

(a) a component (A) comprising, in a physiologically acceptable medium, at least one 1,8-dihydroxy, 1,8-diacyloxy or 1-hydroxy-8-acyloxyanthracene or anthrone, chosen from:
—1,8,9-trihydroxyanthracene or 1,8-dihydroxy-9-anthrone and its dimer,
—1,8,1′,8′-tetrahydroxydianthrone,
—1,8-dihydroxy-9-anthrones substituted in position 10 by groups of formulae:

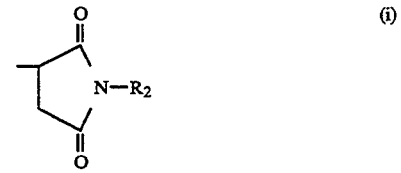 (i)

 (ii)

 (iii)

in which $R_2$ denotes a hydrogen atom, a linear or branched alkyl radical containing from 1 to 8 carbon atoms, a linear or branched mono- or polyhydroxyalkyl radical containing from 1 to 3 carbon atoms, a carbamoyl radical or a phenyl radical, Y and Z denote simultaneously a —$CONR_3R_4$ group or else denote, independently of each other, either a —CONR₃R₄ group or either a $CO_2R_5$ group, with $R_3$, $R_4$ and $R_5$ denoting a hydrogen atom, an alkyl radical containing from 1 to 8 carbon atoms, a mono- or polyhydroxyalkyl radical, optionally interrupted by an oxygen atom, containing from 3 to 8 carbon atoms, a cycloalkyl radical containing from 3 to 6 carbon atoms, or else $R_3$ and $R_4$ taken together form a divalent radical chosen from the following radicals —(CH₂)ₙ— where n is equal to 4 or 5
—(CH₂)₂—O—(CH₂)₂—

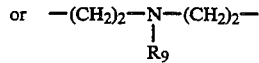

in which $R_9$ denotes a hydrogen atom or a methyl or 2-hydroxyethyl radical.

$R_6$ denotes a $CO_2R_5$, CN, CHO or $CONH_2$ group or else CONH—CH₂OH, in which $R_5$ has the same meaning as that indicated above, and $R_7$ and $R_8$ denote, independently of each other, a hydrogen atom or a methyl radical, as well as their salts and optical isomers, —1,8-dihydroxy-9-anthrone adducts comprising the following divalent radicals in positions 9 and 10:

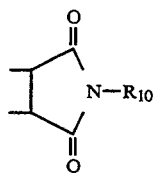

iv)

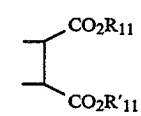

v)

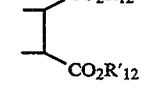

vi)

in which $R_{10}$, $R_{11}$ and $R'_{11}$ denote a hydrogen atom, a linear or branched lower alkyl radical containing from 1 to 8 carbon atoms, a monohydroxy alkyl radical optionally interrupted by one or more oxygen atoms, containing from 2 to 8 carbon atoms, a cycloalkyl radical containing from 4 to 6 carbon atoms, a phenyl radical or a benzyl radical, $R_{12}$ and $R'_{12}$, which are identical or different, denote a hydrogen atom, a linear or branched lower alkyl radical containing from 1 to 8 carbon atoms except for $R_{12}=R'_{12}=CH_3$, a monohydroxyalkyl radical, optionally interrupted by one or more oxygen atoms, containing from 2 to 8 carbon atoms, a phenyl or benzyl radical and the salts of these compounds:

—1,8-dihydroxy-9-anthrones substituted in position 10 by the groups:

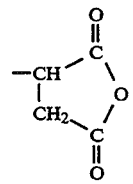

vii)

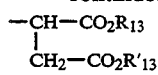

viii)

in which $R_{13}$ and $R'_{13}$, which are identical or different, denote a hydrogen atom or a methyl or ethyl radical, or their isomers, or by the group of formula:

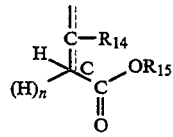

ix)

in which $R_{14}$ denotes a hydrogen atom or the radical $COR'_{15}$, with $R_{15}$ and $R'_{15}$, which are identical or different, denoting a hydrogen atom, a linear or branched alkyl radical containing from 1 to 6 carbon atoms, a cycloalkyl radical containing from 4 to 6 carbon atoms or a benzyl radical, or else $R_{14}$ and $R_{15}$, taken together, form a radical

and n is equal to 0 or 1, as well as their isomers.

—the 10-aryl-1,8-dihydroxy anthrones in which the aryl group corresponds to the following formula:

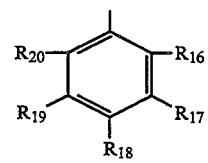

in which $R_{16}$, $R_{17}$, $R_{18}$, $R_{19}$ and $R_{20}$ which are identical or different, denote a hydrogen atom, a halogen atom, the $CF_3$ radical, a hydroxyl group, a lower alkyl or cycloalkyl radical, a lower hydroxyalkyl radical, a lower alkoxy radical, a nitrile group, a radical

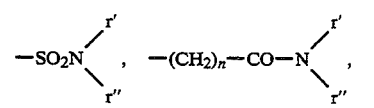

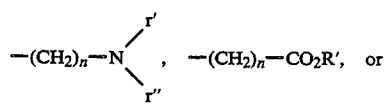

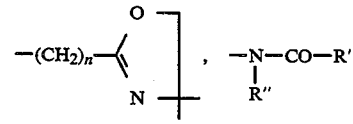

r' and r'', which are identical or different, denote a hydrogen atom or a lower alkyl radical, n is 0 or an integer from 1 to 3 inclusive, and R' and R'' denote a hydrogen atom, a linear or branched lower alkyl radical or an aryl radical, which is or are optionally substituted;

—1,8-diacyloxy-10-acylanthrones of general formula:

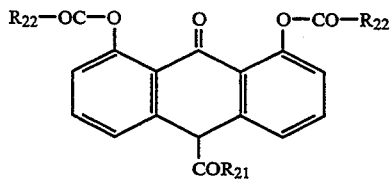

in which:

R$_{21}$ and R$_{22}$, which are identical or different, denote a linear or branched alkyl radical containing from 1 to 15 carbon atoms, a cycloalkyl radical with 3 to 6 carbon atoms, a 2- or 3-furyl radical, a 3- or 4-pyridyl radical, a 2-thienyl radical or an aromatic radical of formula:

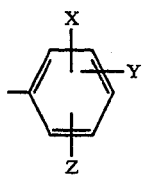

in which X, Y and Z, which are identical or different, denote a hydrogen atom, a lower alkyl radical, a trifluoromethyl radical, a lower alkoxy radical, a halogen atom or a nitro or hydroxyl group, —10-acetyl-1,8,9-triacetoxyanthracene of formula:

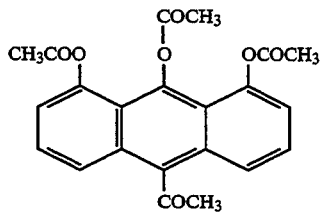

—1-hydroxy-8-acyloxy-10-acylanthrones of general formula:

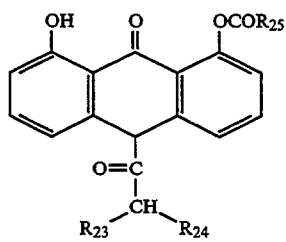

in which:

R$_{23}$ denotes a hydrogen atom or a linear lower alkyl radical;

R$_{24}$ denotes a hydrogen atom, a linear or branched alkyl radical containing from 1 to 17 carbon atoms, a linear or branched alkenyl radical containing from 2 to 17 carbon atoms, or R$_{23}$ and R$_{24}$ taken together form, together with the carbon atom to which they are attached, a cycloalkyl radical containing from 3 to 6 carbon atoms. R$_{25}$ denotes a linear or branched alkyl radical containing from 1 to 18 carbon atoms, a linear or branched alkenyl radical containing from 2 to 18 carbon atoms, a cycloalkyl radical containing from 3 to 6 carbon atoms, a 2- or 3-furyl radical, a 3- or 4-pyridyl radical, a 2-thienyl radical or an aromatic radical of formula:

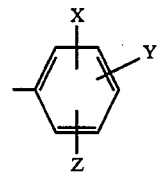

in which X, Y and Z, which are identical or different, denote a hydrogen atom, a lower alkyl radical, a trifluoromethyl radical, a lower alkoxy radical, a halogen atom, a nitro group or a hydroxyl group;

—1,8,9-triacetoxyanthracene of formula:

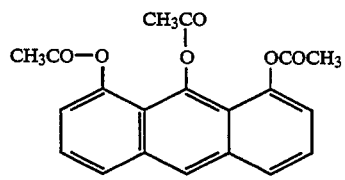

—mono-, di- and triesters of 1,8-dihydroxy-10-phenyl-9-anthrone or 9-anthranol of the following general formula:

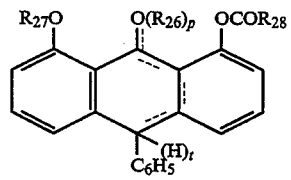

in which:

p is 0 or 1;

when p=0, t=1 and R$_{27}$ denotes a hydrogen atom or —COR$_3$;

when p=1, t=0 and R$_{26}$ and R$_{27}$ denote, independently of each other, a hydrogen atom or —COR$_{28}$;

R$_{28}$ denoting a linear or branched alkyl radical containing from 1 to 17 carbon atoms, a cycloalkyl radical, or a phenyl radical optionally substituted by a lower alkyl, a lower alkoxy, a halogen atom, a nitro group, a —CF$_3$ radical or by a hydroxyl group, and mixtures of said esters.

These compounds are described in greater detail in French Patents and Patent Applications Nos. 2,492,372, 2,492,373, 2,495,934, 2,499,556, 2,565,966, 2,566,722, 2,567,402, 2,567,755, 2,567,756, 2,580,631 and 2,591,222.

(b) a component (B) containing, in a physiologically acceptable medium, at least one pyrimidine derivative corresponding to the formula:

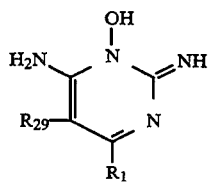

in which $R_1$ denotes a group

in which $R_{30}$ and $R_{31}$, independently of each other, denote hydrogen or an alkyl, alkenyl, alkylaryl or cycloalkyl group; $R_{30}$ and $R_{31}$ can also form a heterocyclic ring with the nitrogen atom to which they are bonded, chosen from aziridinyl, azetidinyl, pyrrolidinyl, piperidyl, hexahydroazepinyl, heptamethyleneimine, octamethyleneimine, morpholine and 4-(lower)alkylpiperazidinyl groups, it being possible for the heterocyclic groups to be substituted on the carbon atoms by 1 to 3 lower alkyl, hydroxyl or alkoxy groups; the group $R_{29}$ is chosen from a hydrogen atom and an alkyl, alkenyl, alkylalkoxy, cycloalkyl, aryl, alkylaryl, arylalkyl, alkylarylalkyl, alkoxyarylalkyl or haloarylalkyl group, as well as the salts of addition to physiologically acceptable acids, the components (A) and (B) forming part of the same single composition or being intended to be employed separately, either simultaneously or successively or offset in time, with a view to inducing and stimulating hair growth and reducing their loss.

In the definition of the compounds employed in the combination in accordance with the invention, the alkyl or alkoxy group preferably denotes a group containing 1 to 4 carbon atoms; the alkenyl group preferably denotes a group containing 2 to 5 carbon atoms; the aryl group preferably denotes phenyl, and cycloalkyl preferably denotes a group containing 4 to 6 carbon atoms.

The preferred compounds of formula (I) are chosen from the compounds in which $R_{29}$ denotes hydrogen, and $R_1$ denotes a group

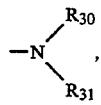

in which $R_{30}$ and $R_{31}$ form a piperidyl ring, as well as their salts, such as, for example, the sulphate.

Among these compounds, the compound which is particularly preferred consists of 6-amino-1,2-dihydro-1-hydroxy-2-imino-4-piperidinopyrimidine, also called minoxidil.

The preferred derivative of 1,8-hydroxy and/or acyloxy anthracene or anthrone is 1,8,9-trihydroxyanthracene or 1,8-dihydroxy-9-anthrone, also known by the name of anthralin or dithranol.

The derivative of 1,8-hydroxy and/or acyloxy anthracene or anthrone is employed in the component (A) in proportions of between 0.01 and 10% by weight, and preferably between 0.1 and 1% by weight and more particularly between 0.1 and 0.5% by weight; the pyrimidine derivative of formula (I) is employed in the component (B) in proportions of between 0.05 and 10% by weight, and preferably between 0.05 and 5% by weight, and particularly between 0.5 and 4% by weight.

The derivative of 1,8-hydroxy and/or acyloxy anthracene or anthrone is employed when the components (A) and (B) are in the same composition, in proportions of between 0.01 and 5% by weight relative to the total weight of the composition, and preferably between 0.10 and 1%, and in particular between 0.1 and 0.5% by weight. In this case, the pyrimidine derivative of formula (I) is employed in the compositions in a proportion of between 0.05 and 6% by weight relative to the total weight of the composition, and preferably between 0.1 and 5%, and in particular between 0.5 and 4% by weight.

The weight ratio of the pyrimidine derivative of formula (I) to the derivative of 1,8-hydroxy and/or acyloxy anthracene or anthrone is preferably between 2/1 and 10/1.

The physiologically acceptable medium for the components (A) and (B) is a medium which may be used in pharmacy or in cosmetics, and may consist of a mixture of water and of one or more solvents or of essentially anhydrous solvents, that is to say those containing less than 1% of water.

These compositions may be pressurized in aerosol devices in the presence of a propellant agent.

The solvents which may be employed are chosen more particularly from $C_1$–$C_4$ lower alcohols such as ethyl alcohol, isopropyl alcohol or tert-butyl alcohol, alkylene glycols such as propylene glycol, mono- and dialkylene glycol alkyl ethers such as, more particularly, ethylene glycol monoethyl ether, propylene glycol monomethyl ether and diethylene glycol monoethyl ether.

The physiologically acceptable media may be thickened or not. Thickening and/or gelling agents which are well known in the state of the art may be employed for thickening. More particularly there may be mentioned, for this purpose, heterobiopolysaccharides such as xanthan gum or scleroglucans, cellulose derivatives, acrylic polymers, crosslinked or not, polyethylene or nylon powder and inorganic thickening agents such as colloidal silica.

The solvents, when employed, are preferably present in proportions of between 1 and 80% by weight, relative to the total weight of the composition.

The thickeners may be employed preferably in proportions of between 0.1 and 5% by weight, and in particular between 0.4 and 3% by weight relative to the total weight of each of the components, when they are employed separately, or relative to the total weight of the composition containing the components (A) and (B).

The compositions consisting either of the components (A) and (B) or of the composition containing the two components (A) and (B) may also contain all the other adjuvants usually employed in compositions intended for topical application in cosmetic or pharmaceutical use, and more particularly preserving agents, complexing agents, colorants, alkalifying or acidifying agents, anionic, cationic, nonionic or amphoteric surface-active agents or mixtures thereof, anionic, cationic, nonionic or amphoteric polymers, and mixtures thereof.

The pH of these compositions may vary between 4 and 9.

The component (A) containing the derivative of 1,8-hydroxy and/or acyloxy anthracene or anthrone may be employed in a particular embodiment with a medium making it possible to avoid an excessively abrupt degradation of the 1,8-hydroxy and/or acyloxy anthracene or anthrone derivative and to preserve it in its active form. To this end, stabilizing agents chosen from glyceric acid, gluconic acid, galacturonic acid, malic acid, citric acid, tartaric acid or tartronic acid may be employed in the physiologically acceptable medium, in a carrier which may consist of isopropyl myristate or palmitate or of glyceryl monostearate.

Another embodiment may consist in employing alkyl esters of fatty acids such as, for example, isopropyl myristate and aromatic esters such as, for example, benzyl salicylate, as the sole carrier for the derivative of 1,8-hydroxy and/or acyloxy anthracene or anthrone. The carrier employed may also be a triglyceride of saturated fatty acids of plant origin, containing from 6 to 18 carbon atoms and especially triglycerides in which the distribution of the fatty acids is as follows:
  —caproic ($C_6$) acid less than 3%
  —caprylic ($C_8$) acid 50 to 80%
  —capric ($C_{10}$) acid 15 to 45%
  —lauric ($C_{12}$) acid less than 5%
and more particularly the products sold under the trade name Miglyol 810 or Miglyol 812 by Dynamit Nobel.

Such compositions are described more particularly in U.S. Pat. Nos. 4,287,214, 4,367,224, 4,316,902 and French Patent Applications 2,520,233, 2,515,045 and 2,569,561.

The component (A) may also be presented in the form of a gel consisting essentially of liquid paraffin, of at least one fatty acid alkyl ester and of a silicone elastomer from the group of polyvinyldimethylsiloxanes, optionally in combination with a silica filler, as described in French Patent 2,570,602.

Another embodiment of the invention may consist in employing the component (A) in the form of a polymeric diffusion matrix consisting of a cellulose ester and of an anhydrous fatty acid alkyl ester as plasticizer, the fatty acid containing 5 to 18 carbon atoms and the linear or branched alkyl radical containing from 3 to 18 carbon atoms, the cellulose esters being chosen particularly from cellulose acetobutyrates and cellulose acetopropionates and having a viscosity of between 0.0038 and 10 Pa s.

The pyrimidine derivatives of formula (I) may be present in the component (B) either in a dissolved form in the physiologically acceptable medium or else totally or partially suspended in this medium, particularly in the form of particles with a particle size of less than 80 microns and particularly less than 20 microns and in particular less than 5 microns.

One embodiment of the invention consists in employing the combination in accordance with the invention in the form of a composition containing the components (A) and (B).

A preferred embodiment of the invention consists in preserving the components (A) and (B) in separate devices and in preparing the composition containing the derivative of 1,8-hydroxy and/or acyloxy anthracene or anthrone and the pyrimidine derivative (I) extemporaneously, immediately before application.

Lastly, another embodiment consists in applying the components (A) and (B) separately, either simultaneously, or successively or offset in time.

In this latter embodiment, it is possible, for example, to apply, in a first stage, a shampoo containing the derivative of 1,8-hydroxy and/or acyloxy anthracene or anthrone and more particularly anthralin and, after having allowed this shampoo to act for 5 minutes to 1 hour, rinsing is carried out, and a lotion based on the pyrimidine derivative of formula (I) is then applied.

Anther embodiment consists in applying a lotion based on the derivative of 1,8-hydroxy and/or acyloxy anthracene or anthrone, and in shampooing, followed by an application of another lotion containing the pyrimidine derivative of formula (I).

In this case, in particular, the combination in accordance with the invention may be packaged in a device with a number of compartments, known as a kit or outfit, in which a first compartment contains the component (A) based on the derivative of 1,8-hydroxy and/or acyloxy anthracene or anthrone and the second compartment contains the component (B) based on the pyrimidine derivative of formula (I).

The process in accordance with the invention is aimed at the therapeutic treatment of hair loss, in so far as it has an effect on the disfunction of the biological mechanisms giving rise to hair growth.

This process may also be considered as a process for cosmetic treatment of hair, endowing it with greater vitality and better appearance.

The examples which follow are intended to illustrate the invention without, however, being limited in character.

EXAMPLE 1

Two compositions (A) and (B) containing the following, respectively, are packaged as a kit:

| Composition (A): Anthralin shampoo packaged in two parts: | |
|---|---|
| 1(A) Gel | |
| Anthralin | 0.60 g |
| Colloidal silica sold by Degussa under the name "Aerosil 200" | 8.00 g |
| Miglyol 812 q.s. | 100.00 g |
| 2(A) Aqueous part | |
| Sodium lauryl ether sulfate oxyethylenated with 2.2 moles of ethylene oxide | 12.00 g |
| Lactic acid q.s. pH = 4 | |
| Water q.s. | 100.00 g |

25% of the gel part (1A) are mixed with 75% of the aqueous part 2(A) at the time of use.

The resulting composition (A) is applied to the scalp. It is left to act for approximately 5 minutes to 1 hour and is then emulsified with water and rinsed off copiously with water.

The composition (B) is then applied:

| Composition (B): Minoxidil lotion | |
|---|---|
| Minoxidil | 1.00 g |
| Propylene glycol | 20.00 g |
| Ethyl alcohol | 50.00 g |
| Water q.s. | 100.00 g |

EXAMPLE 2

Two compositions (A) and (B) containing the following, respectively, are packaged as a kit:

| Composition (A): | |
|---|---|
| Anthralin | 0.40 g |

| Composition (A): | |
|---|---|
| Salicylic acid | 0.40 g |
| Isopropyl myristate q.s. | 100.00 g |

Isopropyl myristate may be replaced with a 50:50 mixture of cetyl octanoate and stearyl octanoate.

This composition (A) is applied to the scalp. After a few minutes to one hour in place, conventional shampooing and rinsing with water are carried out.

A composition (B), as follows, is then applied:

| Composition (B): | |
|---|---|
| Minoxidl | 2.00 g |
| Propylene glycol | 5.00 g |
| Ethyl alcohol q.s. | 100.00 g |

EXAMPLE 3

Two compositions (A) and (B) containing the following, respectively, are packaged as a kit:

| Composition (A): | |
|---|---|
| Anthralin | 0.5 g |
| Isopropyl myristate q.s. | 100.00 g |
| Composition (B): | |
| Minoxidil | 1.33 g |
| Propylene glycol | 20.00 g |
| Ethyl alcohol | 50.00 g |
| Water q.s. | 100.00 g |

An extemporaneous mixture of the two compositions (A) and (B) is prepared, in a proportion of 25% of composition (A) to 75% of composition (B).

The resultant mixture is applied to the scalp. It is left to act for a time and a conventional shampooing is then carried out.

EXAMPLE 4

The following composition is prepared and is applied to the scalp.

| | |
|---|---|
| Anthralin | 0.03 g |
| Minoxidil | 1.00 g |
| Isopropyl myristate | 25.00 g |
| Propylene glycol | 22.50 g |
| Ethyl alcohol q.s. | 100.00 g |

EXAMPLE 5

Two compositions (A) and (B) containing the following, respectively, are packaged as a kit:

| Composition (A): | |
|---|---|
| 1,8-Dihydroxy-9-anthron-10-yl-succinamic acid | 0.14 g |
| Propylene glycol q.s. | 100.00 g |

This composition (A) is applied to the scalp. After a few minutes in place, a composition (B) of the following composition is applied next:

| Composition (B): | |
|---|---|
| Minoxidil | 1.00 g |
| Propylene glycol | 20.00 g |
| Ethyl alcohol | 50.00 g |
| Water q.s. | 100.00 g |

EXAMPLE 6

Two compositions (A) and (B) containing the following, respectively, are packaged as a kit:

| Composition (A): | |
|---|---|
| 1,8-Dihydroxy-10-phenyl-9-anthrone | 9.00 g |
| Colloidal silica sold under the name Aerosil 200 by Degussa | 7.00 g |
| Isopropyl myristate q.s. | 100.00 g |

This gel is applied to the scalp. After a few minutes' to an hour's application, a conventional shampooing and rinsing with water is carried out.

A composition (B), as follows, is applied next:

| Composition (B): | |
|---|---|
| Minoxidil | 2.00 g |
| Propylene glycol | 5.00 g |
| Ethyl alcohol q.s. | 100.00 g |

EXAMPLE 7

Two compositions (A) and (B) containing the following, respectively, are packaged as a kit:

| Composition (A): | |
|---|---|
| 1,8-Dipropionyloxy-10-propionyl-anthrone | 0.5 g |
| Stannous chloride | 0.3 g |
| Isopropyl myristate q.s. | 100.00 g |

This composition is applied to the scalp. After a few minutes' to an hour's application, a conventional shampooing and rinsing with water is carried out.

A composition (B), as follows, is applied next:

| Composition (B): | |
|---|---|
| Minoxidil | 2.00 g |
| Propylene glycol | 20.00 g |
| Ethyl alcohol | 50.00 g |
| Water q.s. | 100.00 g |

EXAMPLE 8

Two compositions (A) and (B) containing the following, respectively, are packaged as a kit:

| Composition (A): | |
|---|---|
| 1,8-Dipivaloyloxy-10-phenyl-anthrone | 0.5 g |
| Stannous chloride | 0.3 g |
| Isopropyl myristate q.s. | 100.00 g |

This composition is applied to the scalp. After a few minutes' to an hour's application, a conventional shampooing and rinsing with water is carried out.

A composition (B), as follows, is applied next:

| Composition (B): | |
|---|---|
| Minoxidil | 2.00 g |
| Propylene glycol | 5.00 g |
| Ethyl alcohol q.s. | 100.00 g |

I claim:

1. A composition comprising a combination intended to induce and to stimulate hair growth and to reduce its loss, comprising:
   (a) an effective amount of a component (A) containing at least one derivative of 1,8-dihydroxy-, 1,8-diacyloxy- or 1-hydroxy-8-acyloxyanthracene or anthrone, in a physiologically acceptable medium,
   (b) an effective amount of a component (B) containing, in a physiologically acceptable medium, at least one pyrimidine derivative corresponding to the formula:

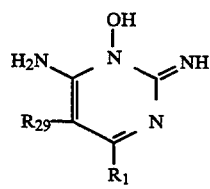

(I)

in which $R_1$ denotes a group

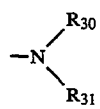

in which $R_{30}$ and $R_{31}$ may, independently of each other, denote hydrogen or an alkyl, alkenyl, alkylaryl or cycloalkyl group; $R_{30}$ and $R_{31}$ can also conjointly, with the nitrogen atom to which they are bonded form a heterocyclic ring selected from the group consisting of aziridinyl, azetidinyl, pyrrolidinyl, piperidyl, hexahydroazepinyl, heptamethyleneimine, octamethyleneimine, morpholinyl, and 4-(lower)alkylpiperazdinyl groups, it being possible for the heterocyclic groups to be substituted on the carbon atoms by 1 to 3 lower alkyl, hydroxyl or alkoxy groups; the group $R_{29}$ denoting a hydrogen atom or an alkyl, alkenyl, alkylalkoxy, cycloalkyl, aryl, alkylaryl, arylalkyl, alkylarylalkyl, alkoxyarylalkyl or haloarylalkyl group, as well as the salts of addition to physiologically acceptable acids, the components (A) and (B) being present in a sole composition or being intended for separate applications, either simultaneous or successive or spaced in time, to hair and to the scalp.

2. The composition according to claim 1, wherein the derivative of 1,8-hydroxy and/or acyloxy anthracene or anthrone is selected from the group consisting of:
   —1,8,9-trihydroxyanthracene or 1,8-dihydroxy-9-anthrone and its dimer,
   —1,8,1',8'-tetrahydroxydianthrone,
   —1,8-dihydroxy-9-anthrones substituted in position 10 by groups of formulae:

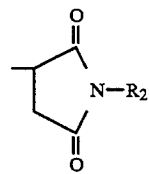

(i)

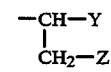

(ii)

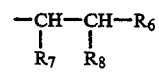

(iii)

in which $R_2$ denotes a hydrogen atom, a linear or branched alkyl radical containing from 1 to 8 carbon atoms, a linear or branched mono- or polyhydroxyalkyl radical containing from 1 to 3 carbon atoms, a carbamoyl radical or a phenyl radical, Y and Z denote simultaneously a $-CONR_3R_4$ group or else denote, independently of each other, either a $-CONR_3R_4$ group or else a $CO_2R_5$ group, with $R_3$, $R_4$ and $R_5$ denoting a hydrogen atom, an alkyl radical containing from 1 to 8 carbon atoms, a mono- or polyhydroxyalkyl radical, optionally interrupted by an oxygen atom, containing from 3 to 8 carbon atoms, a cycloalkyl radical containing from 3 to 6 carbon atoms, or else $R_3$ and $R_4$ taken together form a divalent radical selected from the group consisting of
$-(CH_2)_n-$ where n is equal to 4 or 5 $-(CH_2)_2-O-(CH_2)_2-$, and 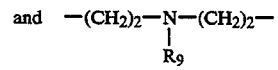

wherein $R_9$ denotes a hydrogen atom or a methyl or 2-hydroxyethyl radical, $R_6$ denotes a $CO_2R_5$, CN, CHO or $CONH_2$ group or else $CONH-CH_2OH$, in which $R_5$ has the same meaning as that indicated above, and $R_7$ and $R_8$ denote, independently of each other, a hydrogen atom or a methyl radical, as well as their salts and optical isomers, —1,8-dihydroxy-9-anthrone adducts comprising the following divalent radicals in positions 9 and 10:

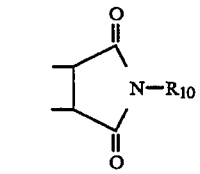

(iv)

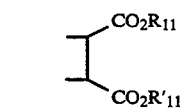

(v)

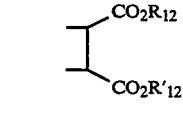

(vi)

in which $R_{10}$, $R_{11}$ and $R'_{11}$ denote a hydrogen atom, a linear or branched lower alkyl radical containing from 1 to 8 carbon atoms, a monohydroxy alkyl radical optionally interrupted by one or more oxygen atoms, containing from 2 to 8 carbon atoms, a cycloalkyl radical containing from 4 to 6 carbon atoms, a phenyl radical or a benzyl radical, $R_{12}$ and $R'_{12}$, which are identical or different, denote a hydrogen atom, a linear or branched lower alkyl radical containing from 1 to 8 carbon atoms except for $R_{12}=R'_{12}=CH_3$, a monohydroxyalkyl radical, optionally interrupted by one or more oxygen atoms, containing from 2 to 8 carbon atoms, a phenyl or benzyl radical and the salts of these compounds:

—1,8-dihydroxy-9-anthrones substituted in position 10 by the groups:

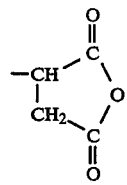

vii)

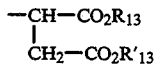

viii)

in which $R_{13}$ and $R'_{13}$, which are identical or different, denote a hydrogen atom or a methyl or ethyl radical, or their isomers, or by the group of formula:

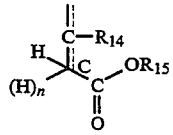

ix)

in which $R_{14}$ denotes a hydrogen atom or the radical $COR'_{15}$, with $R_{15}$ and $R'_{15}$, which are identical or different, denoting a hydrogen atom, a linear or branched alkyl radical containing from 1 to 6 carbon atoms, a cycloalkyl radical containing from 4 to 6 carbon atoms or a benzyl radical, or else $R_{14}$ and $R_{15}$, taken together, form a radical

and n is equal to 0 or 1, as well as their isomers.
—the 10-aryl-1,8-dihydroxy anthrones in which the aryl group corresponds to the following formula:

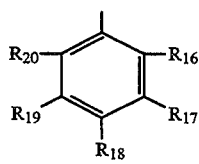

in which $R_{16}$, $R_{17}$, $R_{18}$, $R_{19}$ and $R_{20}$ which are identical or different, denote a hydrogen atom, a halogen atom, the $CF_3$ radical, a hydroxyl group, a lower alkyl or cycloalkyl radical, a lower hydroxyalkyl radical, a lower alkoxy radical, a nitrile group, a radical

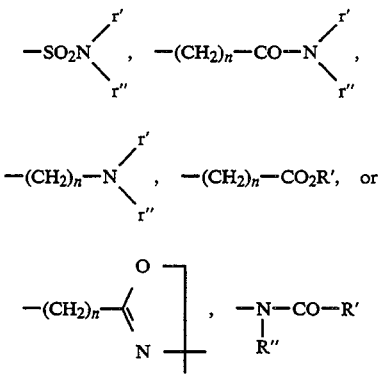

r' and r'', which are identical or different, denote a hydrogen atom or a lower alkyl radical, n is 0 or an integer from 1 to 3 inclusive, and R' and R'' denote a hydrogen atom, a linear or branched lower alkyl radical or an aryl radical, —1,8-diacyloxy-10-acylanthrones of general formula:

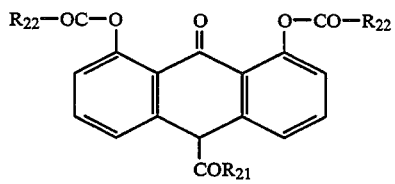

in which:

$R_{21}$ and $R_{22}$, which are identical or different, denote a linear or branched alkyl radical containing from 1 to 15 carbon atoms, a cycloalkyl radical with 3 to 6 carbon atoms, a 2- or 3-furyl radical, a 3- or 4-pyridyl radical, a 2-thienyl radical or an aromatic radical of formula:

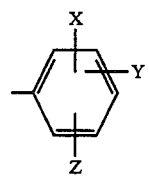

in which X, Y and Z, which are identical or different, denote a hydrogen atom, a lower alkyl radical, a trifluoromethyl radical, a lower alkoxy radical, a halogen atom or a nitro or hydroxyl group;

—10-acetyl-1,8,9-triacetoxyanthracene of formula:

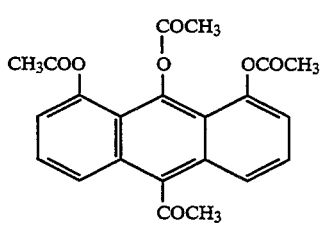

—1-hydroxy-8-acyloxy-10-acyl anthrones of general formula:

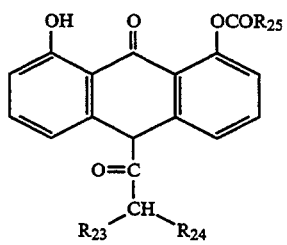

in which:

$R_{23}$ denotes a hydrogen atom or a linear lower alkyl radical;

$R_{24}$ denotes a hydrogen atom, a linear or branched alkyl radical containing from 1 to 17 carbon atoms, a linear or branched alkenyl radical containing from 2 to 17 carbon atoms, or $R_{23}$ and $R_{24}$ taken together form, together with the carbon atom to which they are attached, a cycloalkyl radical containing from 3 to 6 carbon atoms;

$R_{25}$ denotes a linear or branched alkyl radical containing from 1 to 18 carbon atoms, a linear or branched alkenyl radical containing from 2 to 18 carbon atoms, a cycloalkyl radical containing from 3 to 6 carbon atoms, a 2- or 3-furyl radical, a 3- or 4-pyridyl radical, a 2-thienyl radical or an aromatic radical of formula:

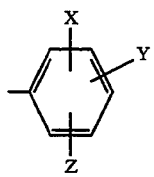

in which X, Y and Z, which are identical or different denote a hydrogen atom, a lower alkyl radical, a trifluoromethyl radical, a lower alkoxy radical, a halogen atom, a nitro group or a hydroxyl group;

—1,8,9-triacetoxyanthracene of formula:

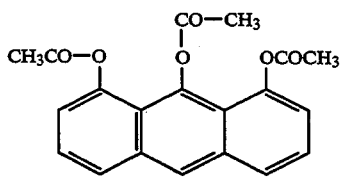

—mono-, di- and triesters of 1,8-dihydroxy-10-phenyl-9-anthrone or 9-anthranol of the following general formula:

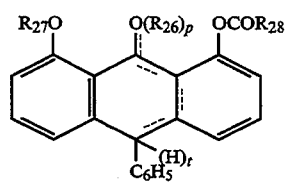

in which:

p is 0 or 1;

when p=0, t=1 and $R_{27}$ denotes a hydrogen atom or —$COR_3$;

when p=1, t=0 and $R_{26}$ and $R_{27}$ denote, independently of each other, a hydrogen atom or —$COR_{28}$;

$R_{28}$ denoting a linear or branched alkyl radical containing from 1 to 17 carbon atoms, a cycloalkyl radical, or a phenyl radical optionally substituted by a lower alkyl, a lower alkoxy, a halogen atom, a nitro group, a —$CF_3$ radical or by a hydroxyl group, and mixtures of said esters.

3. The composition according to claim 1, wherein the pyrimidine derivative is a component of formula (I) in which $R_{29}$ denotes hydrogen and $R_1$ denotes a group

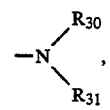

in which $R_{30}$ and $R_{31}$ form a piperidyl ring.

4. The composition according to claim 1, wherein the compound of formula (I) consists of 6-amino-1,2-dihydro-1-hydroxy-2-imino-4-piperidinopyrimidine or minoxidil.

5. The composition according to claim 1, wherein the derivative of 1,8-hydroxy and/or acyloxy anthracene or anthrone consists of 1,8,9-trihydroxyanthracene or 1,8-dihydroxy-9-anthrone or anthralin.

6. The composition according to claim 1, wherein the component (A) contains the derivative of 1,8-hydroxy and/or acyloxy anthracene or anthrone in proportions of between 0.01 and 10% by weight relative to the weight of component (A), and preferably between 0.1 and 1%.

7. The composition according to claim 1, wherein the component (B) contains the compound of formula (I) in proportions of between 0.05 and 10% by weight relative to the total weight of the composition.

8. The composition according to claim 1, wherein the weight ratio of the pyrimidine derivative of formula (I) to the 1,8-hydroxy and/or acyloxy anthracene or anthrone is between 2/1 and 10/1.

9. The composition according to claim 1, under the form of a single composition containing the components (A) and (B) in which the derivative of 1,8-hydroxy and/or acyloxy anthracene or anthrone is present in proportions between 0.01 and 5% by weight relative to the total weight of the composition and that the pyrimidine derivative of formula (I) is present in proportions of between 0.05 and 6% by weight relative to the total weight of the composition.

10. The composition according to claim 1, wherein the physiologically acceptable media consist of one or more anhydrous solvents or a mixture of water and of one or more solvent(s), the solvents are selected from the group consisting of lower alcohols, alkylene glycols or alkylene glycol and dialkylene glycol alkyl ethers.

11. The composition according to claim 1, wherein at least one of the physiologically acceptable media is thickened by means of thickening and/or gelling agents.

12. Combination according to claim 1, wherein at least one of the components (A) and (B) also contains a cosmetically or pharmaceutically acceptable adjuvant selected from the group consisting of preserving agents, complexing agents, colorants, alkalizing agents, acidifying agents, anionic surface-active agents, cationic surface-active agents, nonionic surface-active agents, amphoteric surface-active agents, anionic polymers, cationic polymers, nonionic polymers, amphoteric polymers and mixtures thereof.

13. Process for cosmetic treatment of hair or of the scalp, wherein the components (A) and (B) of the combination defined in claim 1 are applied separately, either simultaneously or successively or spaced in time.

14. Device with a number of compartments or a kit, comprising in a first compartment, a component (A) containing a derivative of 1,8-hydroxy and/or acyloxy anthracene or anthrone defined in claim 1, in a physiologically acceptable medium, and a second compartment containing a component (B) containing a pyrimidine derivative corresponding to formula (I), in a physiologically acceptable medium.

15. The composition comprising a pharmaceutically effective combination for the treatment of hair loss, comprising an effective amount of each the components of the combination of claim 1, wherein said effective amount is effective in inducing and stimulating hair growth and reducing its loss when each of said components is applied to the scalp successively, intermittently, or simultaneously.

16. A method for inducing and stimulating hair growth and reducing its loss comprising applying the pharmaceutical combination of claim 15 to the scalp of an individual afflicted with alopecia.

17. A composition comprising a combination intended to induce and to stimulate hair growth and to reduce its loss, comprising:

(a) an effective amount of a component (A) containing anthralin, in a physiologically acceptable medium, and (b) an effective amount of a component (B) containing in a physiologically acceptable medium, 6-amino-1,2-dihydro-1-hydroxy-2-imino-4-piperidinopyrimidine or minoxidil, components (A) and (B) being intended for separate applications, either simultaneous or successive or spaced in time, to hair and to scalp.

18. The composition according to claim 17, wherein the component (A) contains anthralin in the proportion of between 0.01 and 10% by weight relative to the weight of component (A).

19. The composition according to claim 17, wherein the component (A) contains anthralin in the proportion of between 0.1 and 1% by weight relative to the weight of component (A).

20. The composition according to claim 17, wherein the component (B) contains minoxidil in the proportion of between 0.05 and 10% by weight relative to the total weight of the composition.

21. The composition according to claim 17, wherein the weight ratio of minoxidil to anthralin is between 2/1 and 10/1.

22. Process for cosmetic treatment of hair or scalp, wherein the components (A) and (B) of the combination defined in claim 17 are applied separately, either simultaneously or successively or spaced in time.

23. Device with a number of compartments or a kit, comprising in a first compartment a component (A) containing anthralin in a physiologically acceptable medium, and in a second compartment, a component (B) containing 6-amino-1,2-dihydro-1-hydroxy-2-imino-4-piperidinopyridimide or minoxidil in a physiologically acceptable medium.

* * * * *